United States Patent [19]

Joens et al.

[11] Patent Number: 5,610,059
[45] Date of Patent: Mar. 11, 1997

[54] ETIOLOGICAL AGENT FOR PORCINE ENTERITIS

[75] Inventors: Lynn A. Joens, Tucson, Ariz.; Robert D. Glock, Fort Collins, Colo.

[73] Assignee: University of Arizona, Tucson, Ariz.

[21] Appl. No.: 973,018

[22] Filed: Nov. 9, 1992

[51] Int. Cl.$^6$ .............................. C12N 1/20; C12N 5/00
[52] U.S. Cl. .................. 435/252.1; 435/822; 435/366
[58] Field of Search ............................ 435/240.2, 252.1, 435/822; 424/93.3, 93.4, 93.7

[56] References Cited

U.S. PATENT DOCUMENTS 5,110,589  5/1992  Joens et al. ............................ 424/92

OTHER PUBLICATIONS

Alderton M. R. et al, "J. Comp. Path.," vol. 106(2), 1992 (Mar.), pp. 159–167.
McOrist, S., et al., "Infection & Immunity." vol. 57, #3, Mar. 1989, pp. 957–962.
Gebhart, C. J., et al., "J. of Clin. Microbio.," vol. 29, #5, May 1991, pp. 1011–1015.
Lomax et al Am J Vet Res 43(9) Sep. 1982 pp. 1622–1630.
Mapother, M.E., L.A. Joens, and R.D. Glock. 1987. Experimental reproduction of porcine proliferative enteritis (PPE). Vet. Rec. 121:533–536.
Rowland, A.C. and G.H.K. Lawson. Diseases of Swine. Ed. Lehman, 1986. 6th Edit. Intestinal adenomatosis complex (Porcine proliferative enteropathies). Iowa State Press, pp. 547–556. Section 4, Chap. 47.
Yates, W.D.G., E.G. Clark, A.D. Osborne, C.C. Enweani, O.M. Radostits and A. Theede. 1979. Proliferative hemorrhagic enteropathy in swine: An out–break and review of the literature. Am. Vet J., vol. 20. pp. 261–268.

*Primary Examiner*—David M. Naff
*Assistant Examiner*—Kristin K. Larson
*Attorney, Agent, or Firm*—Quarles & Brady

[57] ABSTRACT

A novel intracellular organism isolated from enterocytes of pigs affected by Porcine Proliferative Enteritis (PPE) may be cultured by passage in a permissive host cell and may be purified from lysates of such cells. On inoculation, the organism of the present invention causes PPE-like symptoms in pigs. The infectious PPE-causing agent may be used to develop a whole organism bacterin or subunit preparation effective to prevent PPE. In addition, the cultured isolate may be used to prepare a battery of therapeutic and diagnostic monoclonal antibodies directed against the PPE-causing agent. Further, by isolating the genetic material from the agent, various useful fusion proteins may be prepared and the genetic makeup of the organism may be determined.

4 Claims, No Drawings

ETIOLOGICAL AGENT FOR PORCINE ENTERITIS

FIELD OF THE INVENTION

The present invention relates generally to bacterial gastroenteric diseases of pigs and in particular to a bacterial agent which causes porcine proliferative enteritis also known as intestinal adenomatosis.

BACKGROUND OF THE INVENTION

Porcine proliferative enteritis (PPE) is a major problem for the U.S. swine industry. PPE is an intestinal disease of pigs characterized by crypt hyperplasia and by the presence of intracellular campyiobacter-like organisms. Recognition of the disease has increased dramatically in the past ten years, with the incidence ranging as high as 20% and losses estimated at $50 million annually in the U.S. alone. Especially alarming is the apparent increase in incidence among the seed stock industry. The disease has been found worldwide and usually affects post-weanling pigs between six and twenty weeks of age. The clinical response of pigs affected with PPE includes intermittent diarrhea, anorexia, marked dullness and apathy, and a wasting syndrome. Death is not uncommon and is frequently associated with hemorrhage effect on intestines. Four different forms of the disease have been described, but the majority of the literature groups the lesions into two forms, acute and chronic, sometimes referred to as necrotic.

In the acute phase of the disease, macroscopic lesions are characterized by the presence of mesenteric and subserosal edema and pronounced reticulation of the serosa. The mucosa and muscle layers are thickened, with the mucosa forming deep longitudinal or transverse folds. The ridges of the folds are often hyperemic with some hemorrhage. Ulceration of the mucosa is occasionally evident with areas of viable mucosa adjacent to the lesion. At a microscopic level, acute lesions are characterized by an acute non-specific inflammation accompanied by hyperemia and edema in the lamina propria, by proliferation of epithelial cells, and by hypertrophy of the ileal musculature. The villi and intestinal crypt structure become irregular, with epithelial cell dysplasia. Crypt abscesses form as crypts become branched and fill with inflammatory cells. The villi and lamina propria become swollen due to the presence of edema and inflammatory cells. The submucosa usually contains lymphatic tissue nodules. The muscle of the ileum, especially the circular layers, may become hypertrophied.

In the chronic stage of the disease, macroscopic lesions are characterized by thickening of the lower small intestine. In some cases, inflammation and epithelial necrosis result in the formation of a fibrinous exudate. The mucosa frequently shows hyperemia and hemorrhage with occasional ulceration. The intestine is usually thickened throughout the lower small intestine, but the mucosal thickening is discontinuous, so that the mucosa is always thinner along the mesenteric attachment. Sometimes, the lumen contains a formed blood clot and the colon may contain tarry feces of mixed blood and digesta. The mucosal surface of the affected small intestine may show little gross damage except for the thickening. Erosions, bleeding points, and ulcers are usually not observed. In addition, the regional lymph nodes are markedly swollen. Microscopic lesions in the chronic stage are characterized by a transmural inflammatory reaction. The mucosa is more distorted with long irregular epithelioid projections. Crypts branch, and produce fissures in the mucosa at the borders of the hyperplastic areas. Ulcers may be seen. Crypt abscesses are also prominent in these areas. Intracellular bacteria, shaped as curved rods, are usually present in the crypt epithelium. The hyperplastic epithelial cells are columnar. Regenerative tissue contains irregularly-formed epithelial cells with a strongly basophilic cytoplasm. Goblet cells are usually infrequent in regeneration areas, but numerous in hyperplastic areas. The lamina propria shows abundant inflammatory cells. Granulomas are occasionally present in ulcerated areas. The submucosa contains dilated lymphatic vessels and fluid-filled tissue spaces. The muscle layers are hypertrophied, with alterations due to the presence of inflammatory cells and fibrin.

The presence of intracellular bacteria in the crypt epithelium of afflicted animals suggests a bacterial etiology for the disease. Although bacteria isolated from such animals are morphologically similar to *Campylobacter spp*, hybridization studies and reproduction experiments using various Campylobacter strains have demonstrated that this organism is not the etiological agent.

Effective PPE control measures have been limited. A basic trial-and-error therapeutic regimen which includes the use of oral and parenteral broad-spectrum antibiotics, antihistamines, corticosteroids, nitroimidazole, and B vitamins, usually becomes quite costly and typically proves ineffective. There has been limited success reproducing PPE using homogenates from affected ileum, and a number of infectious agents have been isolated from PPE-afflicted pigs, though none of these agents has been shown to reproduce the disease after controlled infection. Clearly, the isolation and characterization of the etiological agent of PPE would eliminate some of the trial and error therapeutic practices and would eventually lead to effective control measures using vaccination or medication.

SUMMARY OF THE INVENTION

An intracellular organism isolated from experimentally infected enterocytes produces a PPE-type condition in pigs upon oral inoculation. The isolate may be studied and characterized as to its growth characteristics, surface antigenic properties, and general biology to develop an efficacious vaccine for biological control of PPE.

It is an object of the present invention to provide an easily-manipulated organism capable of repeated passage in vitro and able to cause PPE in a laboratory test animal.

It is another object of the present invention to provide an agent useful for developing prophylactic treatments, including vaccines, against PPE, as well as diagnostic markers for the disease.

Other objects, features and advantages of the invention will become apparent from the following specification.

DESCRIPTION OF THE PREFERRED EMBODIMENT

The present invention is directed to the purification of an intracellular bacterial organism which, after exposure to pigs, causes a PPE-like intestinal disease, and is further directed to uses for the organism in developing vaccines and diagnostic reagents useful in the efforts to eradicate PPE from the domesticated pig population.

In this patent application, the bacterial organism of the present invention will be referred to as the PPE-causing agent. The term PPE-causing agent is intended to encompass all such intracellular organisms that may be propagated by repeated passage in a host cell and that cause macroscopic and microscopic clinical symptoms like those seen in pigs having PPE.

The PPE-causing agent was isolated from infected enterocytes in the intestinal tissue of pigs having PPE lesions. Epithelial cells in the intestinal tissue were detached from the lamina propria by treatment with hyaluronidase. Detached enterocytes were harvested by centrifugation, were resuspended and were treated with antibiotics to kill contaminating gut flora. After washing, the enterocytes were lysed with deoxycholate and were filtered through a 0.65 mm membrane to yield a solution that contained the released PPE-causing agent. The organism has been frozen in liquid nitrogen enterocyte lysates and has been successfully regrown from the frozen cultures by re-inoculation in Henle cells.

To propagate the PPE-causing agent, which appears to be a strict intracellular organism, the filtered lysates containing the PPE-causing agent were used to infect a permissive eukaryotic host, Henle 407, a cell line derived from primary human intestine cells. The infected Henle 407 cells were examined for cytopathic effect (CPE), which was observed 2–4 days after inoculation and was characterized by the elongation and subsequent rounding and sloughing of cells by day 7–10. However, it was possible to sustain the organism by passing 1 ml of supernatant fluid from infected Henle 407 cells onto fresh Henle 407 cells approximately every 7 days.

The infected host Henle 407 cells were used both as a source for obtaining a supply of biologically pure PPE-causing agent and in tests to demonstrate the ability of the PPE-causing agent to induce PPE-like symptoms when inoculated into pigs, which were then observed for clinical signs of PPE. In addition, crude gut homogenates prepared from infected intestinal tissue and normal Henle 407 cells were also administered to piglets as positive and negative controls, respectively.

Results indicated that cells containing the PPE-causing agent were as likely to cause PPE in pigs than homogenates of tissue from infected pigs. Pigs which received uninfected Henle cells were normal at necropsy. In contrast, pigs that received either infected Henle 407 cells or infective gut homogenates exhibited severe diarrhea on day 3 post-inoculation. Three of 4 piglets that received infected Henle 407 cells had gross lesions of PPE at necropsy, as did 5 of 8 piglets that received infective gut homogenates. With one exception, animals having gross lesions also exhibited microscopic lesions. The one exception was a piglet inoculated with uninfected cells which showed mild crypt hyperplasia. Three of 8 piglets that received infective gut homogenates, and 2 of 4 piglets that received infected Henle 407 cells, died due to infection after inoculation.

Transmission electron microscopy (TEM) of negatively stained lysates and scanning electron microscopy (SEM) of fixed lysates made from infected Henle cells revealed high numbers of a slightly curved intracellular organism with approximate dimensions of 0.24–0.27μ×1.4–2.4μ. TEM of thin sections of intestinal tissue from pigs inoculated with infected Henle 407 cells revealed numerous intracellular organisms having similar dimensions. Furthermore, enterocytes from pigs having PPE lesions after inoculation with infected Henle cells appeared totally disarranged or sloughed from the lamina propria.

Having demonstrated the infectivity of the PPE-causing agent, and its ability to induce PPE-like morphological and physiological changes in vivo and in vitro, attention shifts to the envisioned uses for the PPE-causing agent in the arena of PPE prevention and detection. As the PPE-causing agent of the present invention is the first biological isolate able to induce PPE-like disease on inoculation, several envisioned strategies are now made practical which formerly would have been impossible. For example, because the PPE-causing agent may be cultured and purified, it is now possible to develop a bacterin, or inactivated preparation of the PPE-causing agent, using techniques known to the art, which may be administered to pigs at such time during immunological development as to permit the pigs to mount an effective immune response against the agent and against other PPE-causing agents that fall within the scope of the present invention. Bacterins are typically prepared by heat or chemical inactivation of an agent in such manner as to render the agent biologically ineffective, yet antigenically intact.

Alternatively, it is envisioned that various antigenic subunit preparations incorporating proteins from the PPE-causing agent could be prophylactically administered to healthy pigs, which could then mount an immune response against the agent before exposure to a PPE-causing agent. Subunit preparations could be developed in several ways. First, using a classical biochemical approach, purified cell-surface proteins could be prepared from lysates of host cells infected with the PPE-causing agent. The shortcoming of this approach is that it requires exceptionally large quantities of starting material and generates a finite amount of protein from the purified agent.

To produce either a bacterin or a subunit preparation, large-scale cultures of the strict intracellular agent are needed. To determine an optimal host for the agent, other than Henle 407 cells, the agent-containing supernatant from infected Henle 407 cells may be inoculated into a variety of continuous cell line hosts such as, but not limited to, those listed below in Table I.

TABLE I

| Source | Example Cell Lines |
|--------|--------------------|
| Mouse | McCoy, L-929 |
| Monkey | VERO-M, BGM |
| Bovine | EBT, MDBK, EBTh, BFSp |
| Swine | ST, PK-15 |
| Dog | MDCK |
| Hamster | BHK-21 |
| Fish | FHM, EPC, TMB, CCO, BB |

To monitor the growth of the infectious agent in the putative host cell lines, infected cell lines may be screened by immunofluorescent assay which reveals the presence in host cells of antigenic sites rom the infectious agent. Alternatively, other techniques may be used to monitor the growth of the agent in continuous cell lines. For example, western blots directed against a protein of the agent may be used to compare the relative concentration of the protein in lysates from various hosts.

Alternatively, and preferably, with a purified preparation of the PPE-causing agent in hand, one may exploit a host of recombinant DNA techniques directed toward developing subunit vaccines against the PPE-causing agent. The genetic material of the agent may be easily prepared, by standard methods, from lysates of cell cultures infected with the agent. Genes that encode proteins related to known antigenic proteins, or that encode proteins likely to be antigenic in the PPE-causing agent, may be localized using primers developed from consensus sequences of other eubacterial prokaryotes, and may then be subcloned into fusion-protein expression vectors of a type generally known to the art. Such vectors may be expressed in heterologous bacterial, animal or plant cell hosts, or expressed in cell-free enzymatic transcription/translation systems. Antigenic fusion proteins encoded by such vectors may be purified and, if properly post-translationally modified, may be used as prophylactic immunogens in piglets.

Genes identified as expressing antigenic proteins may be amplified and purified for subcloning and DNA sequencing using standard techniques known to the art. Isolated genes or gene fragments may, for example, be cloned directly into bacterial plasmid vectors or may first be ligated to linkers having desirable restriction enzyme cut sites. DNA sequencing data obtained from cloned DNA fragments may be compared to known sequences, such as those of the GenBank repository, in an effort to identify the isolated organism and to more precisely explore the molecular biological bases of PPE and its prevention.

The aforementioned bacterin and subunit preparation methods require indicator reagents that identify antigenic proteins or that detect the presence of the PPE-causing agent in host cells. Such indicators may be obtained from polyclonal hyperimmune sera isolated from piglets that have been exposed to PPE or by developing a battery of monoclonal antibodies directed against the intact PPE-causing agent. Monoclonal antibodies against the antigens of the PPE-causing agent may be produced by lysing the infected host cells, purifying the PPE-causing agent from the lysates by gradient centrifugation, purifying the agent's proteins, and separating the proteins using SDS-PAGE electrophoresis. The SDS-PAGE gel may be stained using either Coomassie blue or silver stain to obtain a profile of the organism's proteins and carbohydrates.

To determine which proteins are antigenic in pigs, and, therefore, useful as immunogens, a portion of the SDS-PAGE gel may be subjected to Western blot analysis using sera from pigs convalescent from PPE, or using hyperimmune sera. Transblotted proteins that bind to serum antibodies may be visualized by sequential addition of an appropriate anti-antibody conjugate labelled with peroxidase and a peroxidase-recognizing color substrate. A more precise determination of antigenic reactivity may be determined by subjecting protein fragments, rather than whole proteins, to SDS-PAGE electrophoresis.

A battery of monoclonal antibodies directed against the Western blot-reactive proteins could then be raised by purifying the reactive proteins from the SDS-PAGE gel and injecting them into appropriate laboratory mice strains known to the art. In due course, activated mouse B-cells and an immortalized cell line could be fused and screened to identify hybridomas that produce antibodies directed to the target protein.

To determine which antigenic epitopes are present on the surface of the PPE-causing agent, Henle 407 cells infected with the agent may be harvested, purified by gradient centrifugation, fixed on a microscope slide, and exposed to a battery of monoclonal antibodies raised against the PPE-causing agent. Then, a fluorescein-labeled anti-immunoglobulin is applied to each slide to visualize the cells to which the monoclonal antibody has bound. Monoclonal antibodies directed particularly to surface antigens of the PPE-causing agent could then be grown in quantity and administered prophylactically to pig populations.

Monoclonal or polyclonal antibodies with activity directed against surface antigens of the PPE-causing agent are useful not only as tools for selecting antigenic fusion proteins created in vitro, but also as possible therapeutic reagents in their own right. Presumably, antibodies directed against surface antigenic determinants of the PPE-causing agent, when administered to piglets, would stimulate at least a temporary immune response against PPE.

Furthermore, antibodies developed against the PPE-causing agent may also be used in the field laboratory to monitor pig populations for the presence of the PPE disease using such assays as ELISA assays or Western blots. ELISA assays and Western blots reveal the presence of a marker protein, such as one carried on the surface of a PPE-causing agent, by binding to the protein an antibody that uniquely recognizes the protein. Such an approach would permit the certification of certain stocks as PPE-free, or, when used as part of a routine pig screening program, could alert the grower to a developing problem in a seed stock population.

Alternatively, known antibodies directed against other obligate intracellular organisms and cross-reactive with PPE-causing agent antigens could be used as cross-reactive markers for PPE and might provide a measure of cross-reactive protection against PPE. The degree of antigenic cross-reactivity with other obligate intracellular organisms such as Rickettsia, Ehrlichia or Chlamydia may be determined by an ELISA assay conducted on french press lysates of the PPE-causing agent using existing monoclonal antibodies directed against antigenic determinants on other obligate intracellular organisms. By adding monoclonal antibodies directed against those organisms to bound lysates containing the PPE-causing agent, cross-reacting antibodies protective against PPE may be revealed.

EXAMPLE 1

Isolation of the PPE-Causing Agent

Intestinal tissue from pigs with PPE lesions was longitudinally opened, washed, and sectioned into 5 cm$^2$ sections. Each section was resuspended into Hank's Balanced Salt Solution (HBSS) and was reacted with N-acetyl cysteine for 60 minutes at 37° C. with constant agitation to remove excess mucus. The mucus-free sections were washed and were resuspended for 1 hour in HBSS containing hyaluronidase to detach epithelial cells from the lamina propria. The sections were then washed and the enterocytes were harvested by centrifugation. The enterocytes were washed and were exposed to gentamicin sulfate and amphotericin B for 24 hours at 4° C. to kill the contaminating gut flora. The treated cells were harvested, washed in HBSS, and lysed with 0.5% deoxycholate for 1 hour at 37° C. with constant agitation to release the intracellular organism. The lysates were passed through a sterile 0.65µ membrane. Filtered lysates were added to confluent monolayers of Henle 407 human intestinal cells in 25 cm$^2$ flasks (1 ml per flask).

The infected cells were examined for cytopathic effect (CPE) during a 10 day incubation period. CPE was observed in Henle 407 cells 3–4 days after inoculation with enterocyte lysate. The CPE usually consisted of cell elongation, followed by rounding and sloughing of cells between days 7–10.

The intracellular nature of the PPE-causing agent was demonstrated by the inability to culture bacterial or fungal agents from the supernatant fluid on various enriched cell-free media at different atmospheres. Accordingly, the agent was sustained by successive inoculations of 1 ml of supernatant fluid from infected Henle 407 cells onto fresh Henle 407 cell monolayers in 25 cm² flasks approximately every 7 days.

EXAMPLE 2

Infectious Nature of the PPE-Causing Agent

The intracellular agent present in enterocyte lysates was propagated in Henle 407 cells to the eighth passage and was then expanded to 20 75 cm² flasks. Normal, uninfected Henle 407 cells were also expanded to inoculate control pigs. Sixteen 3-week old conventional piglets were obtained from a farm that had no prior history of PPE. The piglets were fasted for 24 hours and were inoculated with either crude gut homogenates prepared from infective tissue (n=8), infected Henle 407 cells (n=4), or normal, uninfected Henle 407 cells (n=4). On day 0, the piglets were injected with cimetadine to reduce stomach acidity. On days 0, 1, 2, 13, 14 and 15, the piglets were injected with dexamethasone to marginate neutrophils. The piglets were observed daily for 21 days for clinical signs of PPE.

On day 3 post-inoculation, pigs that received infective gut homogenates or infected Henle 407 cells contracted severe diarrhea. Gross lesions of PPE were present at necropsy in 3 of 4 pigs that received infected Henle 407 cells, and in 5 of 8 pigs that received infective gut homogenates. In contrast, pigs that received uninfected Henle 407 cells were normal at necropsy. All pigs exhibiting gross lesions also had microscopic lesions. In addition, a single pig inoculated with uninfected Henle 407 cells exhibited mild crypt hyperplasia. Deaths were recorded in pigs which received infective gut homogenates (3 of 8) or infected Henle 407 cells (2 of 4).

EXAMPLE 3

Characterization of Infectious Agent

Lysates made from Henle 407 cells infected with enterocyte lysates containing the PPE-causing agent were examined by electron microscopy. Transmission electron microscopy (TEM) of negatively stained infected Henle 407 cell lysates and scanning electron microscopy (SEM) of fixed lysates revealed high numbers of a slightly curved bacterium that was 0.24–0.27μ in width and 1.4–2.4μ in length.

After inoculating pigs with infected Henle 407 cells, thin sections of intestinal tissue examined using TEM contained numerous intracellular organisms which were curved and had dimensions of 0.24–0.26μ width and 1.4–2.0μ length. Enterocytes isolated from pigs inoculated with infected Henle 407 cells and having lesions of PPE appeared totally disarranged or sloughed from the lamina propria.

DEPOSIT

A culture of the PPE-causing agent, hosted in Henle 407 cells has been deposited under the terms of the Budapest Treaty with the American Type Culture Collection located at 12301 Parklawn Drive in Rockville, Md. The culture has been accorded Accession No. 55370, and was deposited Nov. 9, 1992 as a cell line designated Ileitis agent IL-A-. All restrictions on access to this deposited specimen will be removed upon issuance of this patent application.

We claim:

1. A biologically pure culture of a mammalian host cell infected by an obligate intracellular bacterium that causes porcine proliferative enteritis after inoculation into pigs having all of the identifying characteristics of ATCC Accession No. 55370.

2. A biologically pure culture as claimed in claim 1 wherein the mammalian host cell is the human intestinal cell line Henle 407.

3. A biologically pure culture as claimed in claim 1 wherein the obligate intracellular bacterium that causes porcine proliferative enteritis is a bacterium having dimensions in the range of 0.24–0.27 micron×1.4–2.4 micron.

4. A biologically pure culture as claimed in claim 1 wherein the obligate intracellular bacterium that causes porcine proliferative enteritis is isolated from enterocytes of a pig having porcine proliferative enteritis.

\* \* \* \* \*